(12) United States Patent
Israel

(10) Patent No.: US 7,018,334 B2
(45) Date of Patent: Mar. 28, 2006

(54) IMAGING OF A REGION IN A SCATTERING MEDIUM

(76) Inventor: Henry M. Israel, 39 Ben Zakai Street, Bnei Brak 51482 (IL)

( * ) Notice: Subject to any disclaimer, the term of this patent is extended or adjusted under 35 U.S.C. 154(b) by 190 days.

(21) Appl. No.: 10/474,307

(22) PCT Filed: Apr. 8, 2002

(86) PCT No.: PCT/IL02/00288

§ 371 (c)(1),
(2), (4) Date: Oct. 7, 2003

(87) PCT Pub. No.: WO02/082986

PCT Pub. Date: Oct. 24, 2002

(65) Prior Publication Data

US 2004/0181143 A1 Sep. 16, 2004

Related U.S. Application Data

(60) Provisional application No. 60/283,926, filed on Apr. 17, 2001.

(51) Int. Cl.
A61B 8/00 (2006.01)
(52) U.S. Cl. .................................................. 600/443
(58) Field of Classification Search ......... 600/407–472
See application file for complete search history.

(56) References Cited

U.S. PATENT DOCUMENTS 5,999,836 A * 12/1999 Nelson et al. .............. 600/407

* cited by examiner

Primary Examiner—Ali Imam
(74) Attorney, Agent, or Firm—Dekel Patent Ltd.; David Klein

(57) ABSTRACT

A method for imaging a region in a scattering medium, comprising modulating a beam of energy passing through a region of a scattering medium by at least two ultrasonic energy waves having different spatial relationships with said beam of energy so as to form at least two different modulated energy patterns, and detecting and processing said modulated energy patterns to form an image of said region.

4 Claims, 4 Drawing Sheets

IMAGING OF A REGION IN A SCATTERING MEDIUM

CROSS REFERENCE TO OTHER APPLICATIONS

The present application is a national phase application of PCT application PCT/IL02/00288, filed 8 Apr. 2002, which claims priority from U.S. Provisional Patent Application 60/283,926, filed 17 Apr. 2001.

FIELD OF THE INVENTION

The present invention relates generally to forming an image of a region within a scattering medium, related, for example, to visible light tomography systems used in medical imaging.

BACKGROUND OF THE INVENTION

Optical based imaging systems are under study with a goal of providing useful images of structures deep within a body without the use of ionizing radiation. There are four basic ways researchers have been trying to image structures in densely scattering media:

One way to image in a densely scattering medium is by measuring the time-of-flight of photons that travel in the medium and detecting those photons with the shortest travel time. Photons, which experience multiple scattering well outside the beam path, have a longer time-of-flight and may therefore be rejected. This technique has been suggested by Jarry et al. in their paper "Simulation of Laser Tomoscopy in a Heterogeneous Biological Medium", Medical & Biological Engineering & Computation, 1986, 24, 407–414. This technique has been implemented by Takiguchi et al. as described in their paper "Laser Pulse Tomography Using a Streak Camera", Proceedings Image Detection and Quality, July 1986, and by S. Andersson-Engels et al. as described in their paper "Time-resolved Transillumination for Medical Diagnostics", Optics Letters, Vol. 15, No. 21, November, 1990. The technique requires sophisticated pulsed lasers, with pulse times in the picosecond to femtosecond range, and a very fast detection system. With time-of-flight systems, image resolution may be improved at the expense of signal strength.

A second way to image in a densely scattering medium is by the use of coherent light illumination and optical heterodyning detection to reject scattered light. Because of the angular response of a heterodyned detector, the detector may be made sensitive only to light that exits the tissue normal to the detector axis. This technique rejects scattered light, but there is a disadvantage of very low signal strength, since the amount of coherent light in the medium falls off exponentially with the medium thickness. This technique has been demonstrated by researchers at the Thomson CGR research labs and by M. Toida et al. in the Inaba Biophoton Project, Japan. When applied to tissue imaging, the heterodyne and time-of-flight detection techniques are limited to imaging through about 2–3 cm of tissue owing to the low signal levels of the system.

A third way to image in a densely scattering medium is by the use of an optically heterodyned detector in conjunction with sound waves projected into the medium. A system of this type is described in U.S. Pat. No. 5,174,298 to Dolfi and Micheron. Dolfi and Micheron use the fact that a sound wave projected into the medium causes the scattering structures in the medium to vibrate. Light that is scattered by the medium picks up a Doppler shift equal to the medium's vibration frequency. Dolfi and Micheron detect variations in the intensity of this Doppler shift by heterodyning the Doppler modulated light passing through the medium with unmodulated light, then selecting for the Doppler shift frequencies with electronic filters.

A related method is described in U.S. Pat. No. 5,212,667 to Tomlinson, Jr. and Tiemann, wherein coherent light is projected through a scattering medium. The light emerging from the medium is a superposition of a multitude of scattered wavelets, each of which represents a specific scattering path. These wavelets are projected onto a diffuse reflecting surface (the viewing plane of a two-dimensional photodetector array) where they interfere with each other, giving rise to a speckle pattern. By introducing a focused ultrasound pulse into the medium, the positions of the scatterers are changed at a known location (probe region) in the medium, and this causes a change in the speckle pattern. By comparing speckle images before and after the scatterers are moved, the light absorption properties of the probe region may be measured even though multiple scattering interferes with direct imaging of the region.

Despite the directionality of the optical heterodyning procedures employed by Dolfi and Micheron, subsequent scattering in other portions of the scattering medium may undesirably interfere with direct imaging of the Doppler modulated light. Dolfi and Micheron describe ways to reduce this interference. These methods reduce the interference attributable to elastic scattering effects in the medium, but inelastic scattering effects in the medium may still introduce undesirable interference with direct imaging. Furthermore, since the number of photons that travel relatively straight after initial scattering is a negligible fraction of the total number of initially scattered photons, detection sensitivity tends to be poor if subsequently scattered photons remain undetected.

A fourth method to image in a densely scattering medium is by the use of a thermoacoustic response of the medium. An example of this method is described in U.S. Pat. No. 6,292,682 to Kruger. Kruger describes methods and apparatus for measuring and characterizing the localized electromagnetic wave absorption properties of biologic tissues in vivo, using incident electromagnetic waves to produce resultant acoustic waves. The electromagnetic waves are differentially absorbed as the waves pass into and through the tissue, thereby emitting acoustic waves due to the rapid local thermal expansion of the tissue. Multiple acoustic transducers may be acoustically coupled to the surface of the tissue for measuring the acoustic waves. The multiple transducer signals may be combined to produce an image of the absorptivity of the tissue, which image may be used for medical diagnostic purposes. In some embodiments, the transducers may be moved to collect data from multiple locations in order to facilitate imaging.

However, the low-resolution images produced by the Kruger method may be limited by the source pulse width, the acoustic conversion time and the receiver aperture. The method may also be prone to image artifacts due to sampling, processing and multipath interference.

SUMMARY OF THE INVENTION

The present invention seeks to improve the image resolution and measurement quality of absorption in a localized region within a medium where multiple scattering dominates. The present invention may utilize electromagnetic wave energy, such as but not limited to short wavelengths, to image the interaction of another energy wave (e.g., ultrasound) with a scattering medium or objects within a scattering medium, in order to obtain a high two-dimensional spatial resolution.

In the present invention, a coherent electromagnetic source may be projected into a scattering medium. The waves emerging from the medium may be a multitude of scattered wavelets, each representing a specific scattering path. These wavelets may be collected into a receiver and correlated with the original source. The introduction of a focused ultrasound beam into the medium may fix the position of an individual scatter at the intersection of the wave and ultrasound beams, by applying a time resolved modulation to the wave within the (probe region) medium. By demodulation of the wave in time, the location of the scatter may be resolved in one dimension within the focal plane. With the application of a motion of the ultrasound beam, e.g., about the focal point, differing angular projections of the volume may be recorded within a resolution cell. A correlation function (such as a Fast Fourier Transform (FFT)) over a number of angular samples may produce a mapping of the density profile along the resolution cell based on wave absorption properties within the probe region, thus producing a two-dimensional mapping or density image within the probe region. The spatial resolution of this process may be controlled by the process sample time, e.g., pulse width and correlation window time. The attained resolution may be several orders of magnitude smaller then the aperture limit of prior art, resolved, imaging techniques.

In an embodiment of the present invention, an ultrasonic wave may be passed through a scattering medium containing particulates, the ultrasonic (pressure wave) imparting a vibration to the particulates. The particulate motion in turn may impart a modulation or Doppler offset to an electromagnetic wave beam passing through the ultrasonic beam (the intersection being the probe region). The modulation may be extracted from the electromagnetic wave beam and used to locate (time resolve) a region in space. Movement, e.g., rotation, of the source of the ultrasonic wave with respect to the electromagnetic wave beam may impart information to the electromagnetic wave beam as a unique modulation for each increment of movement, e.g., for each angle of rotation. Correlation of the modulation set may produce a density image of the illuminated probe region.

In another embodiment of the invention, a two-dimensional image may be formed by repeating the imaging process for a number of contiguous time-resolved samples. In yet another embodiment, the image may be analyzed to find the statistical distribution of the image (e.g., image vector or image texture), and to establish if the image sample is within norms. One possible implementation of the invention is determination of bone density. Another implementation may be in field of non-destructive testing, as a method of flaw detection.

BRIEF DESCRIPTION OF THE DRAWINGS

The present invention will be understood and appreciated more fully from the following detailed description taken in conjunction with the appended drawings in which.

DETAILED DESCRIPTION OF A PREFERRED EMBODIMENT

Figure 1:
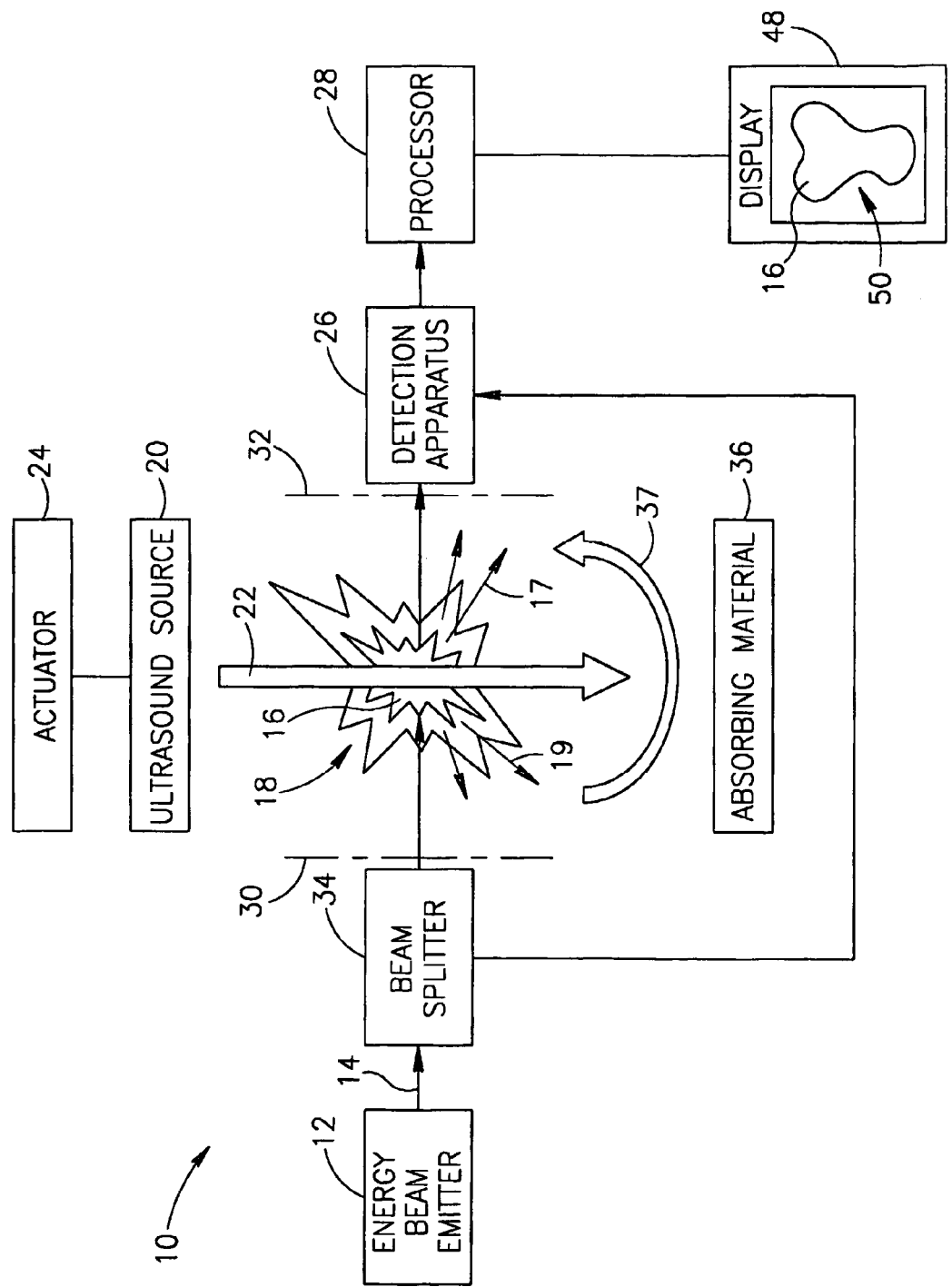
FIG. 1 is a simplified illustration of an imaging system constructed and operative in accordance with a preferred embodiment of the present invention.

Reference is now made to FIG. 1, which illustrates an imaging system 10 constructed and operative in accordance with a preferred embodiment of the present invention.

The imaging system 10 may comprise an energy beam emitter 12, which emits one or more beams of energy 14 into a region 16 of a scattering medium 18. Energy beam emitter 12 may comprise without limitation, a light source, such as but not limited to, a coherent light source (e.g., any suitable laser), X-ray source or other electromagnetic wave energy source. Scattering medium 18 may contain particulates, and may be, for example, living tissue, e.g., bone. Scattering medium 18 may at least partially disperse (scatter) the beam of energy 14 in any direction, such as but not limited to, forward scatter 17 and backward scatter 19.

The imaging system 10 may also comprise an ultrasonic energy source 20, such as an ultrasonic wave transducer. Ultrasonic energy source 20 may be aimed and arranged with respect to energy beam emitter 12 to generate ultrasonic energy waves 22 into region 16. Ultrasonic energy waves 22 may cause vibration of the particulates. The particulate motion or vibration may modulate (e.g., impart a Doppler offset) to the beam of energy 14 passing through the ultrasonic energy waves 22 in region 16 (the intersection being the probe region).

An actuator 24 may be provided to move ultrasonic energy source 20 with respect to the beam of energy 14 emitted by energy beam emitter 12. Actuator 24 may comprise without limitation, a step motor, servomotor, linear actuator, or rotary actuator, and may operate in a closed control servo loop. Actuator 24 may move ultrasonic energy source 20 in any manner, such as but not limited to, translation or rotation. In another example, moving ultrasonic energy source 20 may comprise translating a pattern of electric signals applied to an array of ultrasonic energy sources 20 within an array configuration.

Detection apparatus 26 may be provided for detecting modulated energy patterns produced by modulation of the beams of energy 14 by the ultrasonic energy waves 22. A processor 28 may be provided for processing the modulated energy patterns to form an image of the region 16. Processor 28 may be programmed to process (and reduce) data received from detection apparatus 26 to produce an image. Post processing may be used to determine the details of the region 16 and scattering medium 18 for display.

In one embodiment of the invention, the region 16 of scattering medium 18 may be disposed between first 30 and second 32 opposed surfaces thereof. Ultrasonic energy source 20 may propagate ultrasonic energy waves 22 through scattering medium 18 in a direction substantially parallel to first and second surfaces 30 and 32. By moving ultrasonic energy source 20 with respect to the beam of energy 14, images of the modulated beams exiting scattering medium 18 may be projected onto the second surface 32 so as to form modulated energy patterns. Each modulated energy pattern may correspond to a different view of scattering medium 18.

Figure 3:
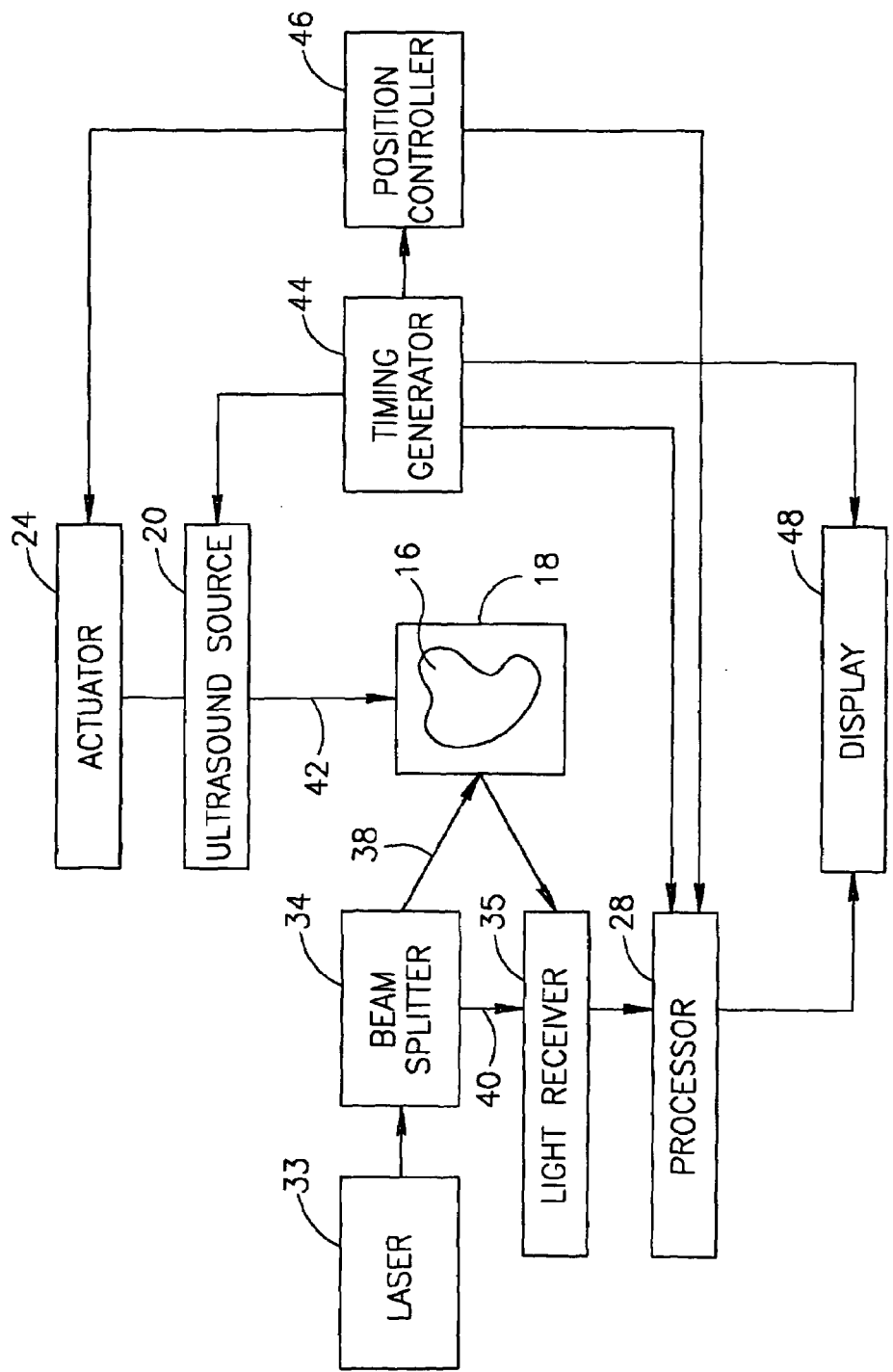
FIG. 3 is a block diagram of an imaging system constructed and operative in accordance with a preferred embodiment of the present invention.

In one embodiment of the present invention, described with reference to FIG. 3, the energy beam emitter 12 may comprise a laser 33, and detection apparatus 26 may comprise a light receiver 35 (e.g., CCD) and a collecting lens (not shown). A beam splitter 34 may cooperate with laser 33 to provide two laser beams: a probing beam 38 and a reference beam 40. An absorbing material 36 (FIG. 1) may be placed outside of the scattering medium 18 to reduce the effect of ultrasound scattering from outside the scattering media being examined. The light receiver 35 may collect the light transmitted through the scattering medium 18 and correlate the probing beam 38 with the reference beam 40. The light receiver 35 may be placed at any desired position to receive the scattered light; either forward or reverse scattered light may be used in the image processing. The light receiver 35 may be moved in any direction, such as but not limited to, the direction of an arrow 37 in FIG. 1.

Accordingly, in one embodiment of the invention, light entering and passing through the scattering medium 18 may be collected as it leaves the scattering medium 18 by an optical system (comprising without limitation, the light receiver 35 and collecting lens), and may be projected onto the light receiver 35 after interfering with the reference beam 40 in the beam splitter 34 to form an optical heterodyne detection. The optical system of such an embodiment may limit the light acceptance angle of the light receiver 35. The receiver spot size may be set by adjustment of the optical system to match the size of the light detector. A line detector array may be used to receive data for more than a single image plane to create a three dimensional image.

The ultrasonic energy source 20 may emit a sonic pulse 42 that travels through the scattering medium 18 as a pressure pulse vs. time. The pulses 42 travel through the scattering medium 18 at the speed of sound for that medium. The pulses 42 may be temporally short, thus confining their length, and the pulses 42 may be focused into a beam such that both transverse dimensions are small. This means that at any particular moment in time, the ultrasonic pulses 42 may be considered to affect significantly only a small volume of the probing beam 38, referred to as the probe region, within the scattering medium 18.

Accordingly, the ultrasonic pulses 42 produce compression/expansion (and/or vibration) at the probe region. The spatial extent of the ultrasonic pulse 42 at the focus point defines the probe region. A timing generator 44, comprising without limitation a timing generator, may be programmed to cause the ultrasonic source 20 to fire pulse 42 into the medium 18, and to open a receive gate over the image area, defined in time. The magnitude of this result may be a function, inter alia, of the light absorption at the probe region, the compressibility of the tissue, and the acoustic power at the probe region.

The timing generator 44 and a position controller 46 may control operation of the actuator 24. A display 48 may be provided to display the processed images of region 16 and scattering medium 18.

Figure 4:
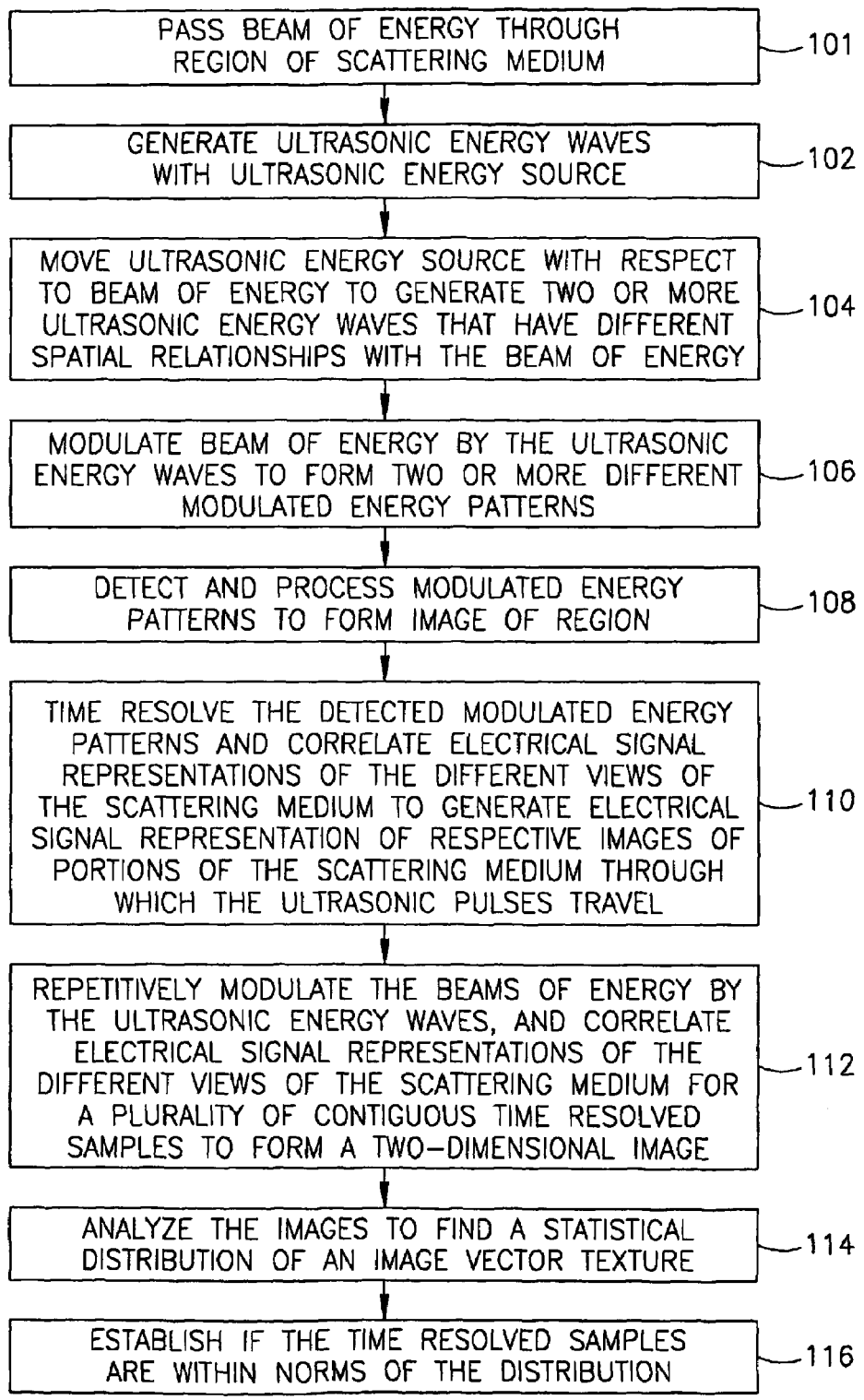
FIG. 4 is a simplified flow chart of a method for imaging in accordance with an embodiment of the invention.

Reference is now made to FIG. 4, which illustrates and summarizes one general method for imaging in accordance with an embodiment of the invention. The description follows with reference as well to FIGS. 1 and 2.

A beam of energy 14 may be passed through the region 16 of scattering medium 18 (step 101, FIG. 4). Ultrasonic energy waves 22 may be generated with ultrasonic energy source 20 (step 102). The ultrasonic energy source 20 may be moved with respect to the beam of energy 14 so as to generate two or more ultrasonic energy waves that have different spatial relationships with the beam of energy (step 104). The beam of energy 14 may then be modulated by the two or more ultrasonic energy waves to form two or more different modulated energy patterns (step 106). The modulated energy patterns may be detected and processed to form an image of region 16 (step 108). Each modulated energy pattern corresponds to a different view of the scattering medium 18, corresponding to the movement (e.g., translation or rotation) of the ultrasonic energy source 20 with respect to the beam of energy 14.

Figure 2:
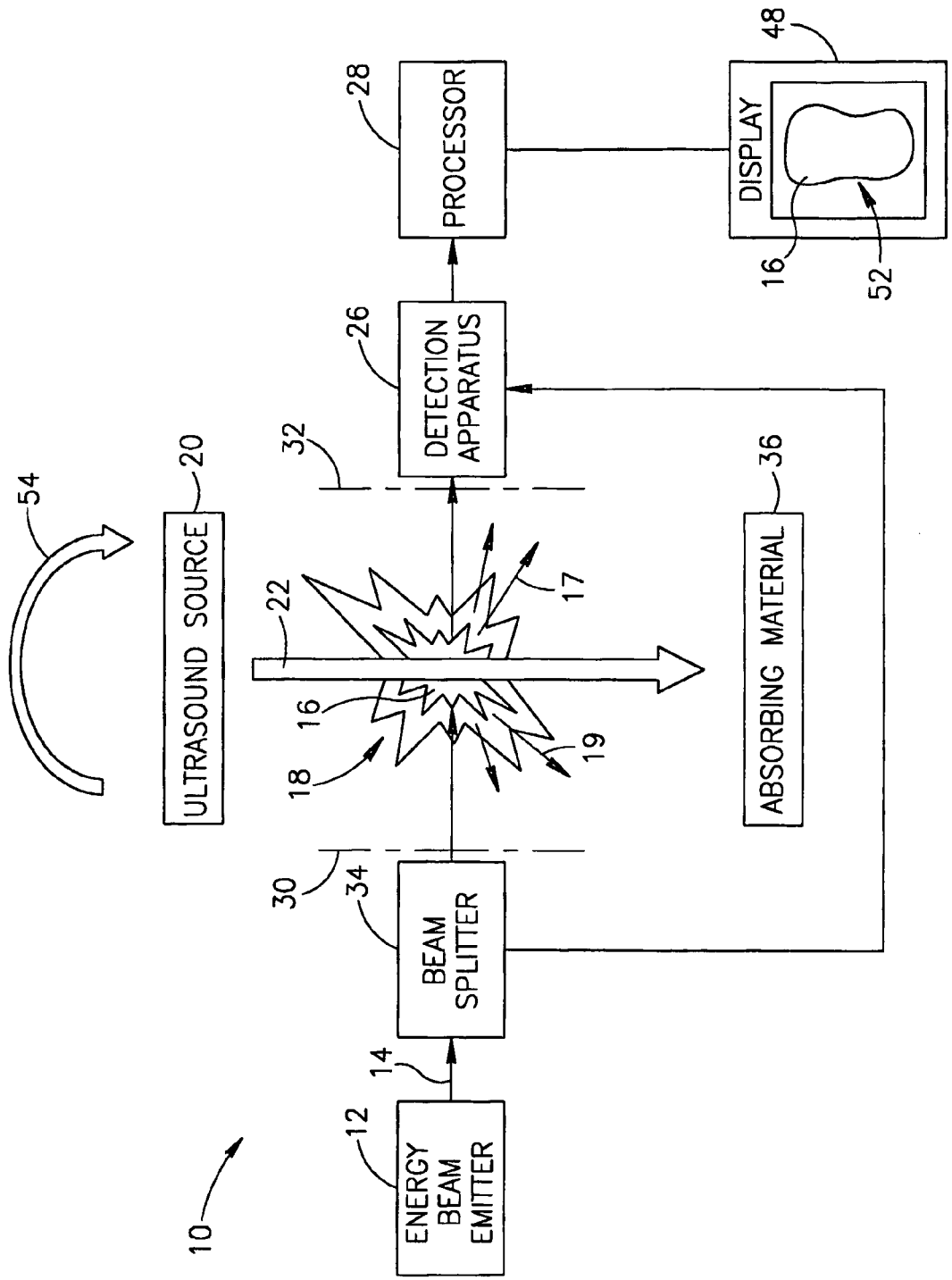
FIG. 2 is a simplified illustration of the imaging system of FIG. 1, illustrating movement (e.g., rotation) of an ultrasound source.

For example, FIG. 1 illustrates a first image 50 of region 16, formed by processing a first view of the scattering medium 18. FIG. 2 illustrates a second image 52 of region 16, formed by moving ultrasonic energy source 20 with respect to the beam of energy 14 in the direction of an arrow 54, and processing the modulated energy pattern produced thereby. The scattering medium 18 and the energy beam emitter 12 may remain stationary.

The processor 28 may time resolve the detected modulated energy patterns and correlate electrical signal representations of the different views of scattering medium 18 to generate electrical signal representations of respective images of portions of scattering medium 18 through which the ultrasonic pulses travel (step 110). The process may repetitively modulate the beams of energy by the ultrasonic energy waves, and correlate electrical signal representations of the different views of scattering medium 18 for a plurality of contiguous time resolved samples to form a two-dimensional image (step 112).

The processor 28 may further analyze the images to find a statistical distribution of an image vector texture (step 114). The processor 28 may establish if the time resolved samples are within norms of the distribution (step 116).

The methods of the present invention have many applications. For example, if the scattering medium comprises tissue and bone, the images may be analyzed to determine the bone density.

In one embodiment of the present invention, the scattering medium 18 may have good ultrasound propagation characteristics and restricted light scattering properties, such as is found in many areas within a normal size human body. The present invention may be used in conjunction with traditional ultrasonic techniques in areas, such as but not limited to, hip and neck bone imaging, to produce clear, two-dimensional, high-resolution images. The invention may thus be used to measure optical absorption versus acoustic impedance change. It is noted that the ultrasound does not have to make a "round trip", but rather needs to travel only one way.

It will be appreciated by person skilled in the art, that the present invention is not limited by what has been particularly shown and described herein above. Rather the scope of the present invention is defined only by the claims that follow:

What is claimed is:

1. A method for imaging a region in a scattering medium, comprising:

modulating a beam of energy passing through a region of a scattering medium by at least two ultrasonic energy waves having different spatial relationships with said beam of energy so as to form at least two different modulated energy patterns; and detecting and processing said modulated energy patterns to form an image of said region, wherein said region of said scattering medium is disposed between first and second opposed surfaces thereof, and said modulating comprises propagating ultrasonic pulses through said scattering medium in a direction substantially parallel to each of said first and second surfaces;

and further comprising projecting onto the second surface of said scattering medium images of the modulated beams exiting said scattering medium so as to form said modulated energy patterns, each modulated energy pattern corresponding to a different view of said scattering medium;

detecting the modulated energy patterns projected on said second surface;

time resolving the detected modulated energy patterns; and correlating electrical signal representations of the different views of said scattering medium to generate electrical signal representations of respective images of portions of said scattering medium through which said ultrasonic pulses travel; and analyzing said images to find a statistical distribution of an image vector texture.

2. The method according to claim 1, and further comprising repetitively modulating said beam of energy by ultrasonic energy waves having different spatial relationships with said beam of energy and correlating electrical signal representations of the different views of said scattering medium for a plurality of contiguous time resolved samples to form a two-dimensional image.

3. The method according to claim 2, and further comprising analyzing said images to find a statistical distribution of an image vector texture and establishing if said time resolved samples are within norms of the distribution.

4. The method according to claim 1, wherein the scattering medium comprises tissue and bone, and further comprising analyzing said images to determine a density of the bone.

* * * * *